(12) United States Patent
Moszner et al.

(10) Patent No.: US 10,781,223 B2
(45) Date of Patent: Sep. 22, 2020

(54) POLYMER MATERIALS WITH SILANE-BASED TRANSFER REAGENTS

(71) Applicants: Ivoclar Vivadent AG, Schaan (LI); Technische Universität Wien, Vienna (AT)

(72) Inventors: Norbert Moszner, Trieseen (CH); Jörg Angermann, Sargans (CH); Urs Karl Fischer, Arbon (CH); Iris Lamparth, Grabs (CH); Yohann Catel, Rans (CH); Robert Liska, Schleinbach (AT)

(73) Assignees: Technische Universität Wien, Vienna (AT); Ivoclar Vivadent AG, Schaan (LI)

( * ) Notice: Subject to any disclaimer, the term of this patent is extended or adjusted under 35 U.S.C. 154(b) by 172 days.

(21) Appl. No.: 16/025,287

(22) Filed: Jul. 2, 2018

(65) Prior Publication Data
US 2019/0010172 A1   Jan. 10, 2019

(30) Foreign Application Priority Data

Jul. 6, 2017  (EP) .................................... 17180115

(51) Int. Cl.
| | | |
|---|---|---|
| *A61K 6/083* | (2006.01) | |
| *C07F 7/18* | (2006.01) | |
| *C08G 77/28* | (2006.01) | |
| *C08L 83/08* | (2006.01) | |
| *C08G 77/20* | (2006.01) | |
| *C08K 9/06* | (2006.01) | |
| *A61K 6/853* | (2020.01) | |
| *A61K 6/887* | (2020.01) | |
| *C08F 230/08* | (2006.01) | |
| *C09C 1/30* | (2006.01) | |
| *C09C 3/12* | (2006.01) | |

(52) U.S. Cl.
CPC ............ *C07F 7/1804* (2013.01); *A61K 6/853* (2020.01); *A61K 6/887* (2020.01); *C07F 7/1892* (2013.01); *C08F 230/08* (2013.01); *C08G 77/20* (2013.01); *C08G 77/28* (2013.01); *C08K 9/06* (2013.01); *C08L 83/08* (2013.01); *C09C 1/3081* (2013.01); *C09C 3/12* (2013.01)

(58) Field of Classification Search
CPC .................... A61K 6/083; A61K 6/887
See application file for complete search history.

(56) References Cited

U.S. PATENT DOCUMENTS

| | | |
|---|---|---|
| 2,694,699 A | 11/1954 | Laakso |
| 5,932,675 A | 8/1999 | Rizzardo et al. |
| 2008/0187499 A1* | 8/2008 | Wolter ............... A61K 6/896 424/49 |
| 2017/0172855 A1 | 6/2017 | Moszner et al. |

FOREIGN PATENT DOCUMENTS

| | | | |
|---|---|---|---|
| DE | 102011050672 A1 | 11/2012 | |
| EP | 3091037 A1 * | 11/2016 | ............... C08K 5/42 |
| WO | 2016177680 A1 | 11/2016 | |

OTHER PUBLICATIONS

Moad, G. et al., "Radical addition-fragmentation chemistry in polymer synthesis," ScienceDirect, Polymer 49 (2008), pp. 1079-1131, Elsevier.
Elias, H.-G., "Macromolecules, vol. 1: Chemical structure and synthesis" Textbook, Sixth, fully revised edition, pp. 299-352, 1999, WILEY-VCH.

* cited by examiner

*Primary Examiner* — Michael F Pepitone
(74) *Attorney, Agent, or Firm* — Ann M. Knab; Thad McMurray

(57) ABSTRACT

Radically polymerizable silane according to the general formula I

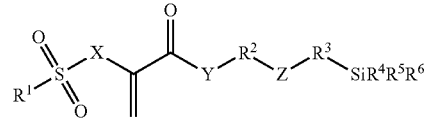

Formula I in which $R^1$ is a linear or branched aliphatic $C_1$-$C_9$-alkyl radical, phenyl or alkylated phenyl radical, $R^2$, $R^3$ independently of each other in each case are absent or are a linear or branched aliphatic $C_1$-$C_{20}$-alkylene radical, which can be interrupted by S or O atoms, $R^4$, $R^5$, $R^6$ independently of each other in each case are —Cl, —O—$CH_3$, —O—$C_2H_5$, —$CH_3$ or —$C_2H_5$, X is $CH_2$ or O, Y is absent, or is O or NR', wherein R' is H or a $C_{1-5}$-alkyl radical, and Z is absent, or is O, NR", —CO—O—, —CO—NR"—, —O—CO—O—, —O—CO—NR"—, or —NR"—CO—NR"—, wherein R" is H or a $C_{1-5}$-alkyl radical and wherein the radicals $R^2$ and $R^3$ cannot be absent at the same time and Z is absent if $R^2$ or $R^3$ is absent, polycondensates based thereon and fillers surface-modified therewith.

23 Claims, No Drawings

POLYMER MATERIALS WITH SILANE-BASED TRANSFER REAGENTS

CROSS-REFERENCE TO RELATED APPLICATIONS

This application claims the benefit of European Patent Application No. 17180115.2 filed on Jul. 6, 2017, which is hereby incorporated by reference in its entirety.

FIELD OF THE INVENTION

The present invention relates to radically polymerizable silanes, which are suitable per se, in the form of polysiloxane condensates or in filler-bound form as chain transfer agents for the monitoring and control of the network structure in radical polymerization.

BACKGROUND

Radical polymers are formed by radical polymerization of one (homopolymers) or more (copolymers) radically polymerizable monomers. Depending on the functionality of the polymerized monomers, linear (in the case of monofunctional monomers) or crosslinked (in the case of di- or multifunctional monomers) polymers are obtained. A great advantage of the radical polymerizations is that, on the one hand, many technically relevant monomers (among others ethylene, vinyl monomers, such as styrene, vinyl chloride, acrylonitrile and vinyl acetate, dienes, (meth)acrylates and (meth)acrylamides) can be radically polymerized and, on the other hand, the radical polymerization can be carried out in bulk (bulk polymerization), solution, suspension or emulsion. To initiate the polymerization, radical-forming initiators are added which form radicals by thermolysis, photolysis or redox reaction.

The radical polymerization proceeds according to a chain propagation mechanism, in which the polymerization-initiating primary radicals formed from the initiator are added to the double bond of the monomers. The initiator radicals formed in this way add many further monomer molecules in a rapid propagation reaction until the propagation of the polymer radicals is terminated by combination or disproportionation and the finished macromolecules form.

Through the addition of chain transfer agents, so-called regulators, the number-average molar mass of the polymer formed can be regulated in a targeted manner (cf. H. G. Elias, Makromoleküle [Macromolecules], Vol. 1, 6th Ed., Wiley-VCH, Weinheim etc. 199, 299-352). The known chain transfer agents include, for example, the mercaptans which form thiyl radicals, which then initiate a new polymerization chain, through transfer of a hydrogen atom.

Double bond-containing reagents which react according to a radical addition-fragmentation chain transfer (AFCT) mechanism have proved particularly useful as chain transfer agents. As AFCT reagents, sulfur compounds such as allyl sulfides, allyl sulfones, dithioesters, dithiocarbamates, xanthates and trithiocarbonates are particularly effective and well investigated (Moad et al., Polymer 49, 1079-1131 (2008)). In addition, reversible AFCT reagents (RAFT reagents), such as e.g. dithioesters, dithiocarbamates, trithiocarbonates or xanthates, are known from controlled radical polymerization (cf. e.g. Moad et al., loc. cit.).

U.S. Pat. No. 2,694,699, which is hereby incorporated by reference, describes the homo- and copolymerization of α-sulfonyloxy acrylates. Alkyl mercaptans can be added as chain regulators.

U.S. Pat. No. 5,932,675, which is hereby incorporated by reference, discloses a process for the production of polymers with low molecular weight by radical polymerization, in which the molecular weight is controlled by the addition of e.g. α-(t-butanethiomethyl)styrene as chain transfer reagent.

EP 2 965 741 A1 and corresponding US 2017122855, which is hereby incorporated by reference, discloses radically polymerizable dental materials which contain allyl sulfones as chain transfer reagent. The materials are characterized by a low polymerization shrinkage stress.

EP 3 090 722 A1 relates to radically polymerizable dental materials which contain vinylsulfonic acid ester as AFCT reagent. The materials have a narrow glass transition range and form homogeneous polymer networks.

The known AFCT reagents as a rule are low-molecular-weight compounds which can leak out of the cured material in the case of incomplete polymerization. In particular, they can be washed out of cured dental materials by saliva, which is undesirable from a toxicological point of view.

SUMMARY

The object of the invention is to provide substances which are suitable as chain transfer reagents for the radical reaction, which do not leak out of the cured material after the polymerization and which are, in particular, not washed out by saliva.

DETAILED DESCRIPTION

This object is achieved according to the invention by silanes of the general formula I, by polysiloxane condensates, which can be obtained by hydrolytic condensation of these silanes, or by fillers which are surface-modified with silanes of the general formula I:

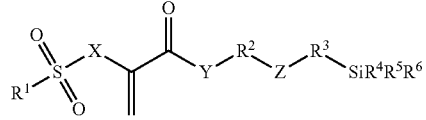

Formula I wherein
$R^1$ is a linear or branched aliphatic $C_1$-$C_9$-alkyl radical, a phenyl or alkylated phenyl radical,
$R^2$, $R^3$ independently of each other in each case are absent or are a linear or branched aliphatic $C_1$-$C_{20}$-alkylene radical, which can be interrupted by S or O atoms,
$R^4$, $R^5$, $R^6$ independently of each other in each case are —Cl, —O—$CH_3$, —O—$C_2H_5$, —$CH_3$ or —$C_2H_5$,
X is $CH_2$ or O,
Y is absent, or is O or NR', wherein R' is H or a $C_{1-5}$-alkyl radical, and
Z is absent, or is O, NR", —CO—O—, —CO—NR"—, —O—CO—O—, —O—CO—NR"—, or —NR"—CO—NR"—, wherein R" is H or a $C_{1-5}$-alkyl radical.

The radicals $R^2$ and $R^3$ cannot be absent at the same time and, if $R^2$ or $R^3$ is absent, Z is preferably also absent.

By an alkylated phenyl radical is meant a phenyl radical which is substituted by 1 to 5 alkyl groups, preferably by 1 alkyl group. $C_{1-10}$-alkyl groups are preferred and in particular $C_{1-5}$-alkyl groups.

Compounds of Formula I, in which the variables have the following meanings, are preferred:

$R^1$ is —$CH_3$, —$C_2H_5$, phenyl or tolyl ($H_3C$-Ph-), in particular p-tolyl, $R^2$, $R^3$ independently of each other in each case are absent or are a linear aliphatic $C_1$-$C_{10}$-alkylene radical, which can be interrupted by O atoms, $R^4$, $R^5$, $R^6$ independently of each other in each case are —O—$CH_3$ or —O—$C_2H_5$, X is $CH_2$ or O, Y is absent or is O, and Z is absent, or is O, —CO—O—, —CO—NH—, —O—CO—O— or —O—CO—NH—.

Silanes of Formula I, in which the variables have the following meanings, are particularly preferred:

$R^1$ is —$CH_3$, —$C_2H_5$, phenyl or tolyl ($H_3C$-Ph-), in particular p-tolyl, $R^2$ is a linear aliphatic $C_2$-$C_8$-alkylene radical, which can be interrupted by O atoms, $R^3$ is absent or is a linear aliphatic $C_1$-$C_6$-alkylene radical, $R^4$, $R^5$, $R^6$ independently of each other in each case are —O—$CH_3$ or —O—$C_2H_5$, X is $CH_2$ or O, Y is O, and Z is absent, or is —CO—NH— or —O—CO—NH—.

The radicals $R^4$, $R^5$ and $R^6$ preferably have the same meaning in all cases.

Formula I extends only to those compounds which are compatible with the theory of chemical valence. The indication that a radical is interrupted by one or more O atoms or S atoms is to be understood to mean that these atoms are inserted in each case into the carbon chain of the radical. These atoms are thus bordered on both sides by C atoms and cannot be terminal. $C_1$ radicals cannot be interrupted.

The compounds of Formula I are active per se as chain transfer agents in the radical polymerization and the use thereof as chain regulators is likewise a subject of the invention. They are preferably used in the form of polycondensates or in a filler-bound form. When compounds of Formula I are mentioned in the following, the polysiloxane condensates and the silanes bound to fillers are thus also meant.

Some polymerization transfer-active Si compounds of Formula I are known and can be easily produced according to known synthesis methods. Thus, allyl sulfone group-containing derivatives (X=$CH_2$) can be produced by addition of iodine compounds to unsaturated derivatives (A) and subsequent HI cleavage (B). Subsequently, a polymerization transfer-active Si compound of Formula I according to the invention can then be obtained by reaction with a suitable silane (C), wherein the protective group technique is optionally to be applied in initial or intermediate stages (Z'=O or NR):

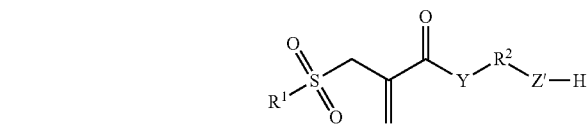

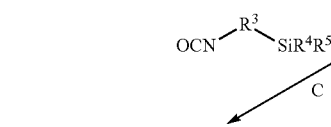

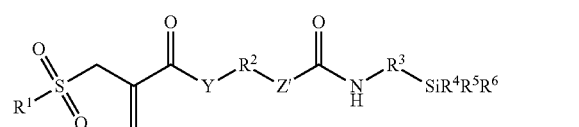

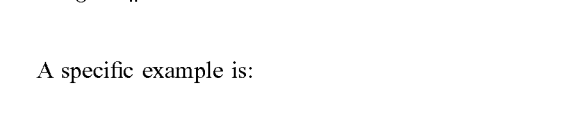

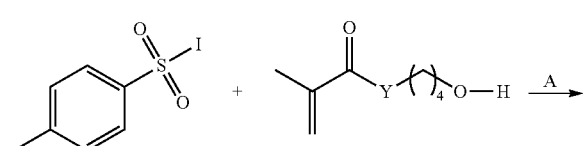

A specific example is:

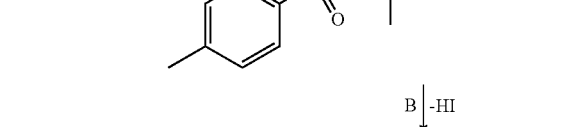

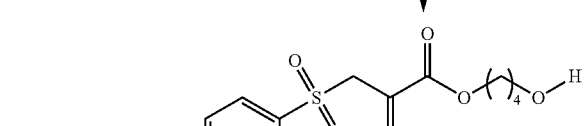

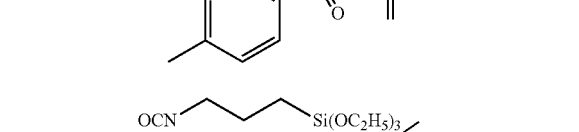

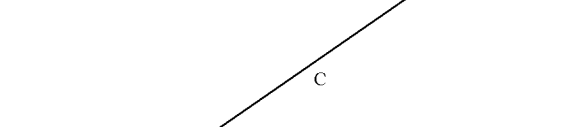

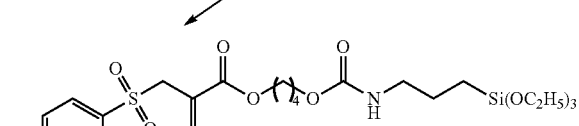

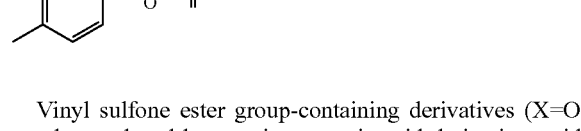

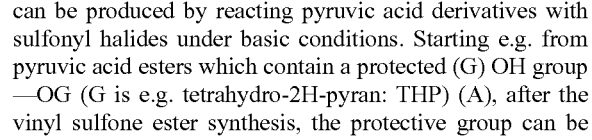

Vinyl sulfone ester group-containing derivatives (X=O) can be produced by reacting pyruvic acid derivatives with sulfonyl halides under basic conditions. Starting e.g. from pyruvic acid esters which contain a protected (G) OH group —OG (G is e.g. tetrahydro-2H-pyran: THP) (A), after the vinyl sulfone ester synthesis, the protective group can be cleaved off (B) and, by further reaction with a suitable silane (C), a polymerization transfer-active Si compound of Formula I according to the invention is obtained (Z'=O or NR):

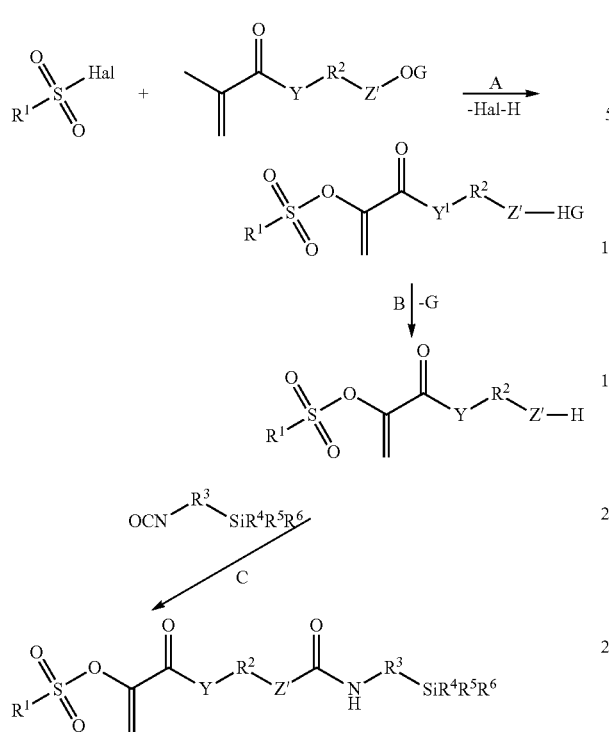
A specific example is:
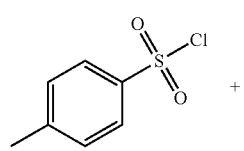
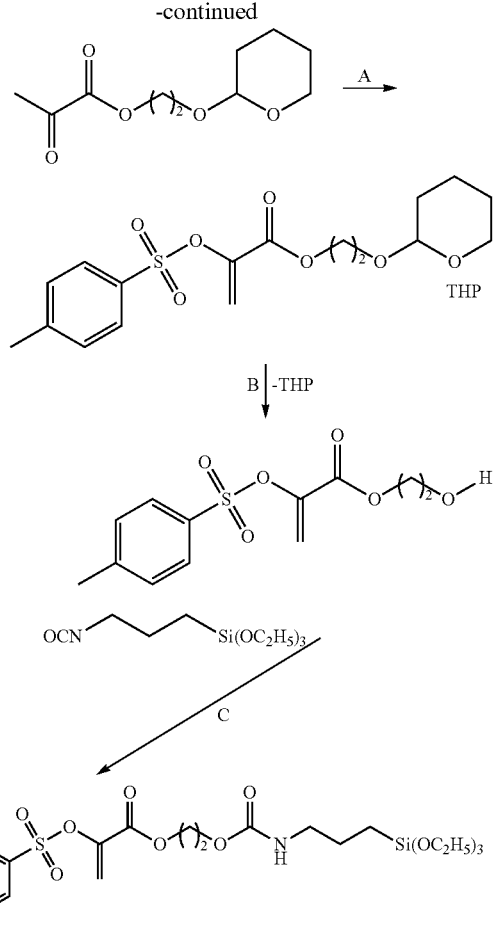
Preferred examples of polymerization transfer-active Si compounds of Formula I according to the invention are:
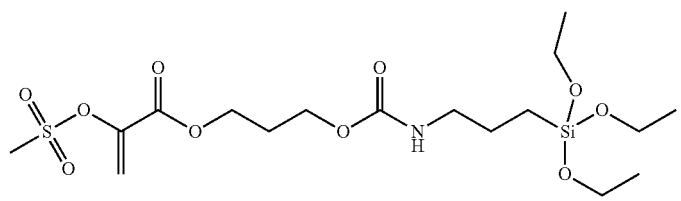
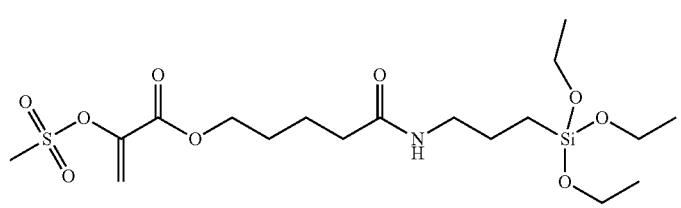
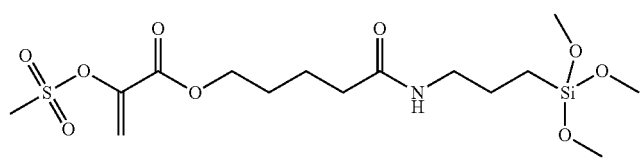

-continued
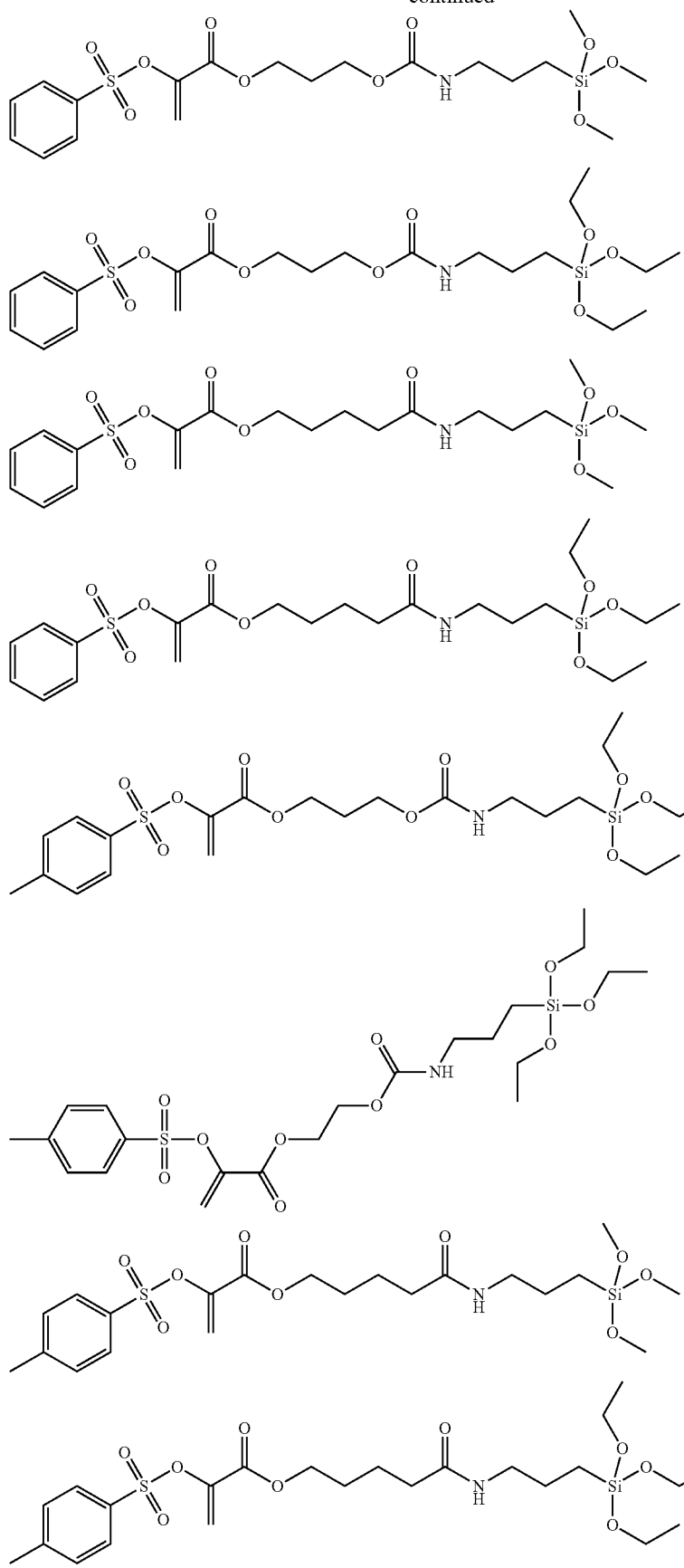

-continued

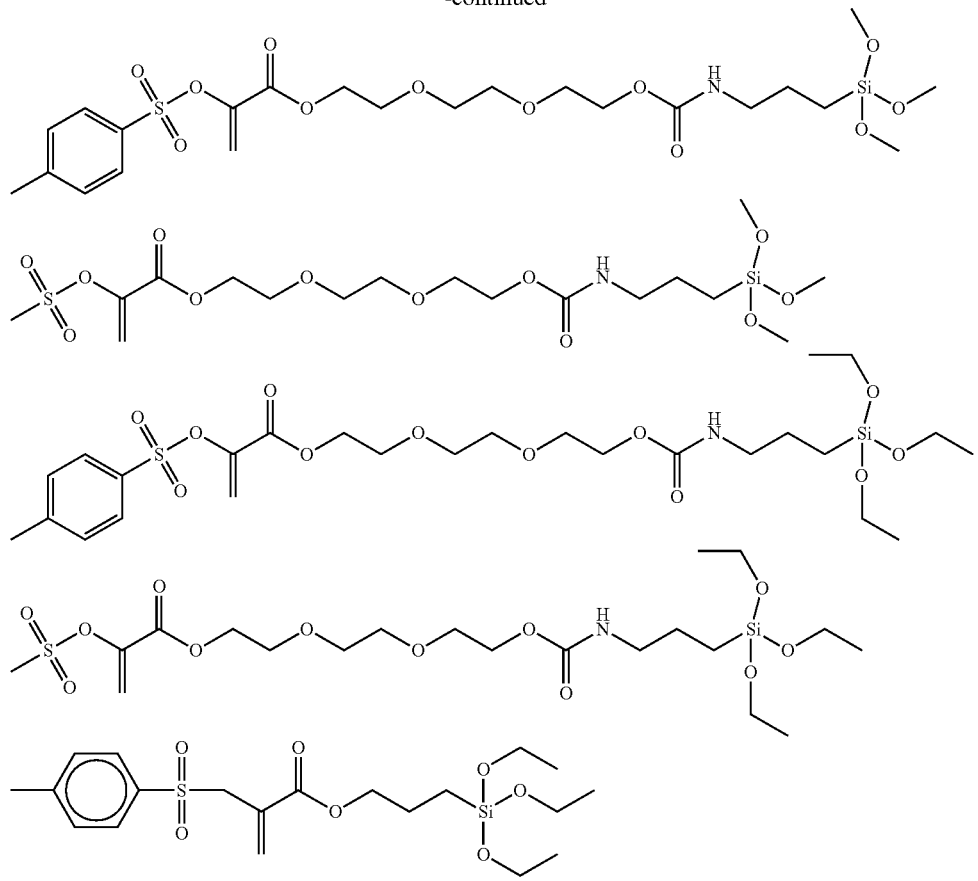

From the polymerization transfer-active Si compounds of Formula I according to the invention, polysiloxane condensates can be produced according to methods known from sol-gel chemistry (cf. monograph: Sol-Gel-Science, C. J. Brinker, G. W. Scherer, Academic Press Inc., Boston etc. 1990), which possess practically no solubility in water. The condensates are preferably produced by hydrolytic condensation.

In the hydrolytic condensation, one or more silanes of Formula I, preferably one silane of Formula I, are mixed in bulk or preferably as a solution in an organic solvent with a stoichiometric amount or an excess of water (preferably >1 to 10 mol water per mol hydrolyzable groups of the silane) and allowed to react. Preferred solvents are acetone, ethanol, methanol, isopropanol, acetic acid ethyl ester, methyl isobutyl ketone, DMF, THF, dioxane or a mixture thereof. In solutions, the silane is preferably diluted with 0.1 to 5 times the volume of solvent. The addition of water takes place in one portion or in portions, wherein the water is preferably diluted with an organic solvent before the addition. The previously named solvents are likewise preferred for this purpose.

The hydrolytic condensation preferably takes place at 0 to 30° C. or at the boiling point of the solvent used (preferably 30 to 140° C.). According to a preferred embodiment of the process, the reaction takes place in two steps. For this purpose, the components are first of all mixed at 0 to 30° C., preferably at room temperature (20° C.), and then warmed to a higher temperature, preferably to 30 to 140° C., to complete the reaction. Then, the reaction mixture is further stirred preferably for a period of from 1 to 120 h, preferably at 20 to 140° C. In the case of alkoxysilanes, the reaction of methoxysilanes takes place more quickly than the reaction of the ethoxysilanes.

To accelerate the reaction, a suitable catalyst, such as e.g. an acid, e.g. acetic acid or hydrochloric acid, or a base, e.g. ammonia, an amine, NaOH, methylimidazole, or ammonium fluoride can advantageously be added. The catalyst is preferably used in a quantity of from 0.001 to 3.0 wt.-% based on the quantity of silane.

After completion of the reaction, the solvent and volatile components are removed, preferably by evaporation in vacuo. The solvent and volatile components are preferably first of all largely evaporated off in a water-jet vacuum and the residue is then further dried in an oil-pump vacuum.

The degree of condensation of the organofunctional polysiloxanes obtained after removal of the solvent and volatile components can be determined by means of $^{29}Si$ NMR spectroscopy. Depending on the degree of condensation and the structure of the silanes according to the invention, liquid or solid polycondensates are obtained. The radicals $R^4$ to $R^6$ determine the structure of the condensates formed. Thus there is a distinction to be drawn between hydrolyzable radicals (—Cl, —O—$CH_3$ and —O—$C_2H_5$) and non-hydrolyzable radicals (—$CH_3$ and —$C_2H_5$). If all of the radicals $R^4$ to $R^6$ are hydrolyzable, a crosslinked condensate (polysiloxane) results on complete conversion, which can be described by the following formula:

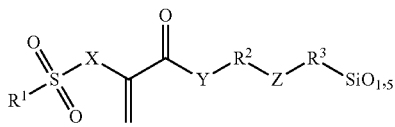

If only two radicals, e.g. $R^4$ and $R^5$, are hydrolyzable, polysiloxanes are obtained which can be described by the following formula:

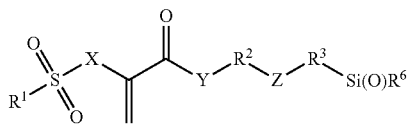

These are linear condensates.

If only one radical, e.g. $R^4$, is hydrolyzable, disiloxanes according to the following formula are obtained:

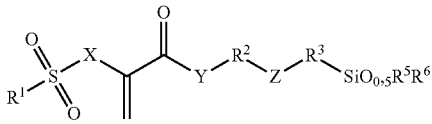

In addition to the production of polysiloxanes, Si compounds of Formula I according to the invention which contain at least one hydrolyzable group $R^4$ to $R^6$ are also suitable for the surface modification of fillers. The modification of the fillers can take place in a manner known per se (cf. e.g. monograph: Silane Coupling Agents, E. P. Pluedemann, 2nd Ed. Plenum Press, New York-London 1991).

As fillers, inorganic particulate fillers, such as powders of quartz and radiopaque barium or strontium aluminium silicate glasses, preferably with an average particle size of from 0.01 to 15 μm, or X-ray opaque fillers, such as ytterbium trifluoride, are preferably suitable. Preferred inorganic particulate fillers are also amorphous spherical nanoparticulate fillers based on oxides, such as fumed silica, precipitated silica, $ZrO_2$, ZnO, $TiO_2$ or mixed oxides made of $SiO_2$, $ZrO_2$ and/or $TiO_2$, preferably with an average particle size of from 10 to 1000 nm. Preferred fillers are furthermore particulate, preferably nanoparticulate, tantalum(V) oxide or barium sulfate as well as mixed oxides of $SiO_2$ with ytterbium(III) oxide or tantalum(V) oxide. In addition, fibrous fillers such as nanofibres, glass fibres, polyamide or carbon fibres can also be used. Particularly preferred fillers are barium or strontium aluminium silicate glasses, mixed oxides made of $SiO_2$ and $ZrO_2$, ytterbium fluoride.

Silanes of Formula I with at least one hydrolyzable radical $R^4$ to $R^6$ react via their silane radical with OH groups on oxidic filler surfaces and are thus bound to the filler. For an optimal surface modification, the filler is preferably dispersed in an organic solvent, particularly preferably ethanol, acetone, isopropanol, methanol, acetic acid ethyl ester, THF or a mixture thereof, mixed with one or more silanes of Formula I, preferably with one silane of Formula I, and water (preferably 1 to 10 mol based on the quantity of silane used) and preferably also with a catalyst (preferably 0.001 to 2 mol-% based on the quantity of silane used) and stirred. The reaction is preferably carried out at a temperature of from 0° C. to 100° C., for example at 0° C. to room temperature (20° C.) or at increased temperature (30 to 100° C.). Analogously to the production of the condensates, the water is preferably diluted with solvent before the addition, wherein the solvents named above are preferred for this purpose. Preferred catalysts are acids, e.g. acetic acid or hydrochloric acid, bases, e.g. ammonia or amines, or ammonium fluoride. The reaction mixture is stirred until completion of the reaction, preferably for 1 to 20 hours, e.g. overnight (approx. 15 hours). The surface-modified filler is subsequently separated off, preferably filtered off, then preferably washed with pure solvent and subsequently dried to constant weight. The degree of surface modification can be determined from the residue on ignition or an elemental carbon analysis.

The silanes of Formula I, the polysiloxane condensates obtained therefrom and the fillers surface-modified therewith have polymerization transfer-active allyl sulfone or vinyl sulfone ester groups and can be used in the polymerization of radically polymerizable monomers and in particular of multifunctional (meth)acrylates, mixtures thereof or of mixtures of multifunctional (meth)acrylates with mono (meth)acrylates for the monitoring and control of the network structure.

According to the invention it was found that the silanes of Formula I enable an effective control of the polymerization even if they are bound to fillers or are present as condensate. This is surprising because the mobility of the regulating molecules in the reaction medium is greatly limited by bonding them into larger units.

The polymerization transfer-active groups in compounds of Formula I result in polymers with a narrower glass transition, i.e. the glass transition takes place in a narrower temperature range. Moreover, more homogeneous polymer networks are obtained, i.e. networks which are characterized in that they have a narrower distribution of the molar mass between the crosslinking points. This has the advantage that chain tensions can be better relieved by relaxation processes. Correspondingly, the polymerization shrinkage stress can also be reduced during the curing of the materials, which is a great advantage for a dental application, e.g. as filling material.

The silanes of Formula I have radically polymerizable double bonds via which they can react with radically polymerizable monomers, with the result that they are bound into the polymer network during curing. Moreover, the condensates and the surface-modified fillers are practically insoluble in water, with the result that they are not washed out of the cured materials, for example by saliva.

The silanes of Formula I are preferably used in the form of their condensates and in a filler-bound form. However, they can also be used as such for the production of radically polymerizable materials. In this case, the silane groups make binding to present fillers possible in situ.

The silanes, condensates and fillers according to the invention are suitable for the production of polymers, plastics, thermosetting plastics and composite materials/composites e.g. for technical applications, for the production of medical devices, for example for surgery or ophthalmology, and in particular for the production of dental materials.

For this purpose, the silanes of Formula I and in particular the condensates thereof or fillers surface-modified therewith can be combined with different types of radically polymerizable monomers. Particularly preferred are materials which contain at least one mono- or multifunctional (meth)acrylate as radically polymerizable monomer. By monofunctional (meth)acrylates are meant compounds with one, by polyfunctional (meth)acrylates compounds with two or more, preferably 2 to 4, radically polymerizable groups. According to a quite particularly preferred embodiment, the compositions according to the invention contain at least one dimethacrylate or a mixture of mono- and dimethacrylates. Materials which contain mono- and multifunctional (meth) acrylates as radically polymerizable monomer are particularly suitable as dental materials, wherein for materials which are cured intraorally, methacrylates are preferred.

Examples of particularly suitable mono- or multifunctional (meth)acrylates are methyl, ethyl, 2-hydroxyethyl, butyl, benzyl, tetrahydrofurfuryl or isobornyl (meth)acrylate, p-cumylphenoxyethylene glycol methacrylate (CMP-1E), bisphenol A di(meth)acrylate, Bis-G(M)A (an addition product of (meth)acrylic acid and bisphenol A diglycidyl ether), ethoxylated or propoxylated bisphenol A di(meth) acrylate, such as e.g. the bisphenol A dimethacrylate SR-348c (Sartomer) with 3 ethoxy groups, or 2,2-bis[4-(2-(meth)acryloxypropoxy)phenyl]propane, UD(M)A (an addition product of 2-hydroxyethyl (meth)acrylate and 2,2,4-trimethylhexamethylene diisocyanate), di-, tri- or tetraethylene glycol di(meth)acrylate, trimethylolpropane tri (meth)acrylate, pentaerythritol tetra(meth)acrylate, as well as glycerol di- and tri(meth)acrylate, 1,4-butanediol di(meth)acrylate, 1,10-decanediol di(meth)acrylate ($D_3MA$) or 1,12-dodecanediol di(meth)acrylate.

In addition, the materials according to the invention preferably also contain at least one initiator for the radical polymerization. To initiate the radical photopolymerization, benzophenone, benzoin as well as derivatives thereof or α-diketones or derivatives thereof, such as 9,10-phenanthrenequinone, 1-phenyl-propane-1,2-dione, diacetyl or 4,4'-dichlorobenzil, are preferably used. Camphorquinone (CQ) and 2,2-dimethoxy-2-phenyl-acetophenone are particularly preferably used and quite particularly preferably used are α-diketones in combination with amines as reducing agent, such as e.g. 4-(dimethylamino)-benzoic acid ethyl ester (EDMAB), N,N-dimethylaminoethyl methacrylate, N, N-dimethyl-sym.-xylidine or triethanolamine. Norrish type I photoinitiators are also suitable, preferably acyl- of the bisacylphosphine oxides, monoacyltrialkyl- or diacyldialkylgermanium compounds, such as e.g. benzoyltrimethylgermanium, dibenzoyldiethylgermanium or bis(4-methoxybenzoyl)diethylgermanium (MBDEGe). Mixtures of the different photoinitiators can advantageously also be used, such as e.g. bis(4-methoxybenzoyl)diethylgermanium in combination with camphorquinone and 4-dimethylaminobenzoic acid ethyl ester.

To initiate the radical polymerization, azo compounds, such as 2,2'-azobis(isobutyronitrile) (AIBN) or azobis-(4-cyanovaleric acid), or peroxides, such as dibenzoyl peroxide, dilauroyl peroxide, tert-butyl peroctoate, tert-butyl perbenzoate or di-(tert-butyl) peroxide are particularly suitable. To accelerate the initiation by means of peroxides, combinations with aromatic amines can also be used. Preferred redox systems are combinations of benzoyl peroxide with amines, such as N,N-dimethyl-p-toluidine, N,N-dihydroxyethyl-p-toluidine, p-dimethylaminobenzoic acid ethyl ester or structurally related systems. In addition, redox systems consisting of peroxides and reducing agents such as e.g. ascorbic acid, barbiturates or sulfinic acids or combinations of hydroperoxides with reducing agents and catalytic metal ions, such as e.g. a mixture of cumene hydroperoxide, a thiourea derivative and copper(II) acetylacetonate, are also suitable for the dual curing.

According to a preferred embodiment, the materials according to the invention additionally contain organic or preferably inorganic particulate filler, particularly preferably one or more inorganic particulate fillers. Mixtures which contain monomers and fillers are called composites.

Fillers based on oxides with a particle size of from 0.010 to 15 m, such as $SiO_2$, $ZrO_2$ and $TiO_2$ or mixed oxides made of $SiO_2$, $ZrO_2$, ZnO and/or $TiO_2$, nanoparticulate or microfine fillers with a particle size of from 10 to 300 nm, such as fumed silica or precipitated silica as well as glass powder with a particle size of from 0.01 to 15 μm, preferably from 0.2 to 1.5 μm, such as quartz, glass ceramic or X-ray opaque glass powder of e.g. barium or strontium aluminium silicate glasses, and X-ray opaque fillers with a particle size of from 0.2 to 5 μm, such as ytterbium trifluoride, tantalum (V) oxide, barium sulfate or mixed oxides of $SiO_2$ with ytterbium(III) oxide or tantalum(V) oxide, are particularly suitable. Fibrous fillers, such as nanofibres or whiskers can also be used.

Unless otherwise stated, all of the particle sizes herein are weight-average particle sizes.

The fillers are divided according to particle size into macrofillers and microfillers. Macrofillers are obtained by grinding quartz, X-ray opaque glasses, borosilicates or ceramic, are of a purely inorganic nature and mostly consist of splinter-shaped particles. Macrofillers with an average particle size of from 0.2 to 10 μm are preferred. Fumed $SiO_2$ or precipitated silica are preferably used as microfillers, or also mixed oxides, e.g. $SiO_2$—$ZrO_2$, which can be obtained by hydrolytic cocondensation of metal alkoxides. The microfillers preferably have an average particle size of from approx. 5 to 100 nm.

To improve the bond between the filler particles and the crosslinked polymerization matrix, $SiO_2$-based fillers can be surface-modified with (meth)acrylate-functionalized silanes. An example of such silanes is 3-(meth)acryloyloxypropyltrimethoxysilane. To surface-modify non-silicate fillers, e.g. of $ZrO_2$ or $TiO_2$, functionalized acidic phosphates, such as e.g. 10-(meth)acryloyloxydecyl dihydrogen phosphate, can also be used.

Optionally, the compositions used according to the invention can contain further additives, above all stabilizers, dyes, microbiocidal active ingredients, fluoride ion-releasing additives, expanding agents, optical brighteners, plasticizers or UV absorbers.

The materials according to the invention preferably contain the following components:
(a) 1 to 50 wt.-%, preferably 2 to 40 wt.-% and particularly preferably 3 to 30 wt.-% of at least one silane of Formula I, preferably at least one condensate of one or more silanes of the general formulae (I) and/or at least one filler which is surface-modified with at least one silane of Formula I,
(b) 0.01 to 5 wt.-%, preferably 0.1 to 5 wt.-% and particularly preferably 1.0 to 3.0 wt.-% of at least one initiator for the radical polymerization,
(c) 5 to 80 wt.-%, preferably 10 to 60 wt.-% and particularly preferably 10 to 50 wt.-% of at least one radically polymerizable monomer.

In addition, the materials preferably also contain
(d) 1 to 80 wt.-% of at least one filler different from component (a).

The fill level is geared to the desired intended use of the material. Filling composites preferably have a filler content of 50-80 wt.-% and composite cements of 10-70 wt.-%. When a filler-bound silane of Formula (I) is used as component (a), these quantities relate to the total amount of (a) and (d).

In addition, the materials can advantageously contain (e) 0 to 5 wt.-%, preferably 0 to 3 wt.-% and particularly preferably 0.2 to 3 wt.-% of additive(s).

Unless otherwise stated, all of the quantities herein relate to the total mass of the materials. The preferred quantity ranges can be chosen separately in each case.

Materials are particularly preferred which consist of the named components. Furthermore, those materials are preferred in which the individual components in each case are selected from the above-named preferred and particularly preferred substances. In addition, materials are particularly preferred which, in addition to the silanes of Formula I, condensates based thereon or fillers surface-modified therewith, contain no other chain regulators.

The materials according to the invention are suitable in particular as dental materials, in particular as dental cements, filling composites and veneering materials as well as materials for the production of prostheses, artificial teeth, inlays, onlays, crowns and bridges. They are characterized in that, after curing, the silanes of Formula I on the one hand are bound into the polymer network via a radically polymerizable group and on the other hand are bound to a filler via a silane group or are integrated into a condensate, with the result that the silanes do not leak out of the cured material and in particular are not washed out on contact with saliva. In addition, the materials have a reduced polymerization shrinkage stress (PSS) and an improved impact strength.

The dental materials are suitable primarily for intraoral application by the dentist for the restoration of damaged teeth, i.e. for therapeutic application, e.g. as dental cements, filling composites and veneering materials. However, they can also be used extraorally, for example in the production or repair of dental restorations, such as prostheses, artificial teeth, inlays, onlays, crowns and bridges.

A further subject of the invention are homo- and copolymers which can be obtained by polymerization of dental materials according to the invention. Polymers of this type can, for example, be processed using cutting processes to form prostheses or artificial teeth. They are preferably available in the form of cylindrical or disc-shaped blanks.

The materials according to the invention are suitable in addition for the production of shaped bodies which can be produced, e.g. by means of casting, compression moulding or 3D printing. The improved impact strength in particular allows these materials to come to the same level as common thermoplastics. In addition, the small delay in curing is advantageous for 3D printing. The materials according to the invention can therefore be processed very well by stereolithography or 3D printing.

In addition, the invention relates to the use of silanes of Formula I, condensates thereof and fillers surface-modified therewith as chain transfer agents in radical polymerization or for the monitoring or control of the network structure in the radical polymerization in particular of (meth)acrylates.

The invention is explained in more detail below with reference to examples.

EMBODIMENT EXAMPLES

Example 1

Synthesis of the Silane 2-(toluene-4-sulfonyloxy)-acrylic acid 2-[N-(3-triethoxysilyl)-propylcarbamoyloxyethyl] ester 1$^{st}$ Stage: Pyruvic Acid 2-(tetrahydropyran-2-yloxy)-ethyl Ester

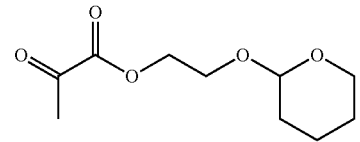

A solution of pyruvic acid (17.61 g, 0.20 mol), 2-(tetrahydro-2H-pyran-2-yloxy)ethanol (29.24 g, 0.20 mol) and N,N-dimethylaminopyridine (0.60 g, 5.0 mmol) in dichloromethane (200 ml) was mixed in portions at −5° C. with N,N'-dicyclohexylcarbodiimide (45.39 g, 0.22 mol). The suspension was stirred for 2 h at −5° C. and then at ambient temperature. After 20 h, the reaction mixture was diluted with n-heptane (200 ml) and filtered through silica gel. The filtrate was concentrated in a rotary evaporator and the crude product was purified by means of column chromatography (SiO$_2$, n-heptane/ethyl acetate 2:1). 32.78 g (0.152 mol; 76%) of a yellowish liquid was obtained.

$^1$H-NMR (CDCl$_3$, 400 MHz): δ=1.47-1.65 (m, 4H; CH$_2$—CH$_2$—CH$_2$), 1.66-1.87 (m, 2H; CH$_2$—CH$_2$—CH$_2$), 2.48 (s, 3H; CH$_3$), 3.48-3.56 (m, 1H; O—CH$_2$), 3.70-3.78 (m, 1H; O—CH$_2$), 3.81-3.89 (m, 1H; O—CH$_2$), 3.95-4.02 (m, 1H; O—CH$_2$), 4.38-4.49 (m, 2H; COO—CH$_2$), 4.66 (t, 1H; J=3.3 Hz; O—CH—O).

$^{13}$C-NMR (CDCl$_3$, 100.6 MHz): δ=19.0 (CH$_2$), 25.2 (CH$_2$), 26.6 (CH$_3$), 30.2 (CH$_2$), 61.9 (O—CH$_2$), 64.4 (O—CH$_2$), 65.2 (O—CH$_2$), 98.5 (O—CH—O), 160.6 (C=O), 191.4 (C=O).

IR (pure): 2943 (w), 2872 (w), 1730 (vs), 1442 (w), 1385 (w), 1357 (w), 1299 (m), 1202 (w), 1184 (w), 1124 (vs), 1077 (s), 1033 (s), 1020 (s), 907 (w), 894 (w), 871 (m), 813 (m), 718 (w) cm$^{-1}$.

Analysis calculated for C$_{10}$H$_{16}$O$_5$: C, 55.55; H, 7.46. Found: C, 55.89; H, 7.25.

2$^{nd}$ Stage: 2-(toluene-4-sulfonyloxy)-acrylic Acid 2-(tetrahydropyran-2-yloxy)-ethyl Ester

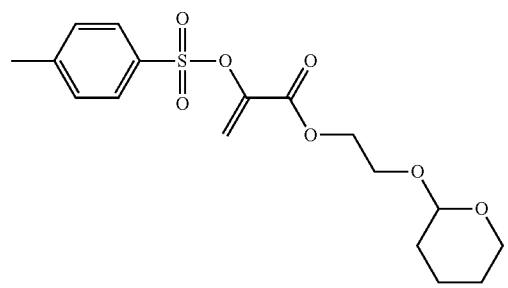 [SMILES: C=C(OS(=O)(=O)c1ccc(C)cc1)C(=O)OCCOC1CCCCO1]

To a solution of pyruvic acid 2-(tetrahydropyran-2-yloxy)-ethyl ester (32.58 g, 0.151 mol), p-toluenesulfonyl chloride (28.72 g, 0.151 mol) and N,N-dimethyl-aminopyridine (0.90 g, 7.5 mmol) in dichloromethane (250 ml), triethylamine (27.45 g, 0.271 mol) was added dropwise. The reaction mixture was stirred for 20 h at ambient temperature, washed with water (3×100 ml) and saturated aqueous NaCl solution (100 ml), dried over anhydrous sodium sulfate, filtered and concentrated in a rotary evaporator. The crude product was purified by means of column chromatography (SiO$_2$, n-heptane/ethyl acetate 4:1). 24.26 g (65.5 mmol; 43%) of a yellowish oil was obtained.

$^1$H-NMR (CDCl$_3$, 400 MHz): δ=1.47-1.86 (m, 6H; CH$_2$—CH$_2$—CH$_2$), 2.46 (s, 3H; CH$_3$), 3.48-3.55 (m, 1H; O—CH$_2$), 3.59-3.65 (m, 1H; O—CH$_2$), 3.83-3.91 (m, 2H; O—CH$_2$), 4.22-4.33 (m, 2H; O—CH$_2$), 4.63 (t, 1H; J=3.3 Hz; O—CH—O), 5.64 (d, 1H; J=2.2 Hz; =CH), 6.16 (d, 1H; J=2.2 Hz; =CH), 7.36 (d, 2H; J=8.2 Hz; Ar—H), 8.85 (d, 2H; J=8.2 Hz; Ar—H).

$^{13}$C-NMR (CDCl$_3$, 100.6 MHz): δ=19.1 (CH$_2$), 21.6 (CH$_3$), 25.2 (CH$_2$), 30.3 (CH$_2$), 61.9 (O—CH$_2$), 64.5 (O—CH$_2$), 64.9 (O—CH$_2$), 98.6 (O—CH—O), 117.0 (=CH$_2$), 128.5 (Ar—CH), 129.6 (Ar—CH), 132.4 (Ar—C), 142.9 (=C), 145.5 (Ar—C), 160.8 (C=O).

IR (pure): 2943 (w), 2871 (w), 1736 (m), 1639 (w), 1597 (w), 1494 (w), 1453 (w), 1378 (m), 1295 (m), 1194 (s), 1179 (s), 1151 (s), 1125 (vs), 1091 (s), 1078 (s), 1035 (m), 1019 (m), 985 (m), 958 (s), 905 (m), 872 (m), 814 (s), 780 (m), 711 (vs), 696 (s), 661 (s) cm$^{-1}$.

Analysis calculated for C$_{17}$H$_{22}$O$_7$S: C, 55.12; H, 5.99; S, 8.66. Found: C, 55.73; H, 6.06; S, 8.39.

3$^{rd}$ Stage: 2-(toluene-4-sulfonyloxy)-acrylic acid 2-hydroxyethyl Ester

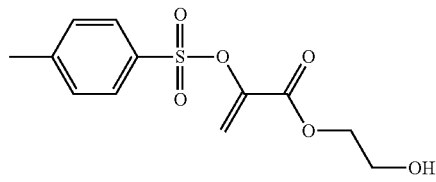 [SMILES: C=C(OS(=O)(=O)c1ccc(C)cc1)C(=O)OCCO]

A solution of 2-(toluene-4-sulfonyloxy)-acrylic acid 2-(tetrahydropyran-2-yloxy)-ethyl ester (24.16 g, 65.2 mmol) in methanol (250 ml) was mixed with Amberlyst® 15 hydrogen form (10.0 g) and stirred at ambient temperature. After 20 h, the reaction mixture was filtered and the filtrate concentrated in a rotary evaporator. The crude product was purified by means of column chromatography (SiO$_2$, dichloromethane/ethyl acetate 4:1). 10.57 g (36.9 mmol; 57%) of a yellowish oil was obtained.

$^1$H-NMR (CDCl$_3$, 400 MHz): δ=2.46 (s, 3H; CH$_3$), 2.76 (t, 1H; J=6.5 Hz; OH), 3.78-3.84 (m, 2H; O—CH$_2$), 4.25-4.30 (m, 2H; O—CH$_2$), 5.50 (d, 1H; J=2.3 Hz; =CH), 6.18 (d, 1H; J=2.3 Hz; =CH), 7.37 (d, 2H; J=8.2 Hz; Ar—H), 8.83 (d, 2H; J=8.2 Hz; Ar—H).

$^{13}$C-NMR (CDCl$_3$, 100.6 MHz): δ=21.6 (CH$_3$), 60.3 (O—CH$_2$), 67.4 (O—CH$_2$), 117.5 (=CH$_2$), 128.3 (Ar—CH), 129.8 (Ar—CH), 132.0 (Ar—C), 142.9 (=C), 145.8 (Ar—C), 161.0 (C=O).

IR (pure): 3545 (br w), 1735 (s), 1639 (m), 1596 (m), 1494 (w), 1373 (s), 1294 (s), 1194 (s), 1178 (s), 1144 (vs), 1089 (s), 1018 (w), 956 (s), 918 (m), 877 (m), 815 (s), 781 (s) 710 (vs), 695 (s), 660 (s) cm$^{-1}$.

Analysis calculated for C$_{12}$H$_{14}$O$_6$S: C, 50.34; H, 4.93; S, 11.20. Found: C, 50.37; H, 4.97; S, 11.09.

4$^{th}$ Stage: 2-(toluene-4-sulfonyloxy)-acrylic acid 2-[N-(3-triethoxysilyl)-propylcarbamoyloxyethyl] ester

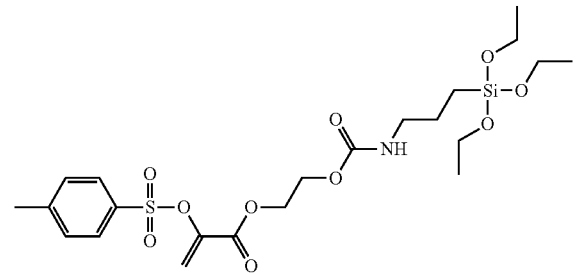 [SMILES: C=C(OS(=O)(=O)c1ccc(C)cc1)C(=O)OCCOC(=O)NCCC[Si](OCC)(OCC)OCC]

To a solution of 2-(toluene-4-sulfonyloxy)-acrylic acid 2-hydroxyethyl ester (10.47 g, 36.6 mmol) and dibutyltin dilaurate (0.13 g, 0.2 mmol) in acetone (20 ml), 3-(triethoxysilyl)propyl isocyanate (9.04 g, 36.6 mmol) was added dropwise. The reaction solution was stirred at ambient temperature and, after 24 h, concentrated in a rotary evaporator. The crude product was purified by means of column chromatography (SiO$_2$, n-heptane/ethyl acetate 1:1). 11.56 g (21.1 mmol; 58%) of a yellowish oil was obtained.

$^1$H-NMR (CDCl$_3$, 400 MHz): δ=0.58-0.68 (m, 2H; Si—CH$_2$), 1.22 (t, 9H; J=7.0 Hz; CH$_2$—CH$_3$), 1.57-1.68 (m, 2H; CH$_2$—CH$_2$—CH$_2$), 2.46 (s, 3H; CH$_3$), 3.11-3.22 (m, 2H; O—CH$_2$), 3.82 (q, 6H; J=7.0 Hz; CH$_2$—CH$_3$), 4.17-4.24 (m, 2H; O—CH$_2$), 4.25-4.32 (m, 2H; O—CH$_2$), 5.15-5.30 (m, 1H; NH), 5.65 (d, 1H; J=2.5 Hz; =CH), 6.15 (d, 1H; J=2.5 Hz; =CH), 7.37 (d, 2H; J=8.4 Hz; Ar—H), 8.84 (d, 2H; J=8.4 Hz; Ar—H).

$^{13}$C-NMR (CDCl$_3$, 100.6 MHz): δ=7.4 (Si—CH$_2$), 18.0 (CH$_3$), 21.5 (CH$_3$), 23.0 (CH$_2$), 43.2 (CH$_2$), 58.2 (O—CH$_2$), 61.6 (O—CH$_2$), 63.9 (O—CH$_2$), 117.3 (=CH$_2$), 128.3 (Ar—CH), 129.6 (Ar—CH), 132.3 (Ar—C), 142.6 (=C), 145.5 (Ar—C), 155.8 (C=O), 160.5 (C=O).

$^{29}$Si-NMR (CDCl$_3$, 79.5 MHz): δ=−45.7.

IR (pure): 3339 (br w), 2974 (w), 2928 (w), 2887 (w), 2928 (w), 1727 (s), 1639 (w), 1597 (w), 1524 (w), 1444 (w), 1380 (m), 1296 (m), 1241 (m), 1180 (s), 1195 (s), 1156 (s), 1076 (vs), 957 (s), 815 (m), 779 (m), 713 (m), 696 (w), 663 (w) cm$^{-1}$.

Analysis calculated for C$_{22}$H$_{35}$NO$_{10}$SSi: C, 49.51; H, 6.61; N, 2.62; S, 6.01. Found: C, 50.44; H, 6.72; N, 2.95; S, 5.80.

Example 2

Hydrolytic Condensation of 2-(toluene-4-sulfonyloxy)-acrylic acid 2-[N-(3-triethoxysilyl)-propylcarbamoyloxyethyl] ester

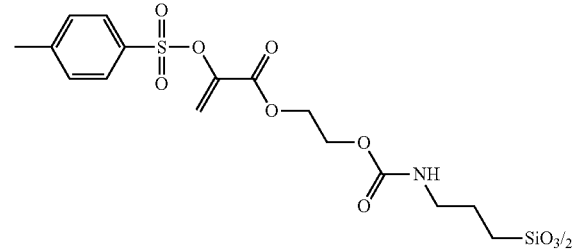

A solution of 2-(toluene-4-sulfonyloxy)-acrylic acid 2-[N-(3-triethoxysilyl)-propylcarbamoyloxyethyl] ester (5.34 g, 10.0 mmol) in ethanol (48.0 g) was mixed with hydrochloric acid (0.5 M, 0.54 g, 55.8 mmol) and stirred for 72 h at room temperature. The solvent was removed and the residue was dried at 60° C. in a fine vacuum. 4.09 g (9.6 mmol; 96%) of a highly viscous yellowish oil that is insoluble in water was obtained.

$^1$H-NMR (CDCl$_3$, 400 MHz): δ=0.50-0.77 (m, 2H; Si—CH$_2$), 1.50-1.73 (m, 2H; CH$_2$—CH$_2$—CH$_2$), 2.45 (s, 3H; CH$_3$), 3.03-3.24 (m, 2H; O—CH$_2$), 4.15-4.38 (m, 4H; O—CH$_2$), 5.49-5.54 (m, 1H; =CH), 6.06-6.18 (m, 1H; =CH), 7.34 (d, 2H; J=7.8 Hz; Ar—H), 7.82 (d, 2H; J=7.8 Hz; Ar—H).

Example 3

Synthesis of the Silane 3-(triethoxysilyl)-propyl-2-(tosylmethyl) acrylate

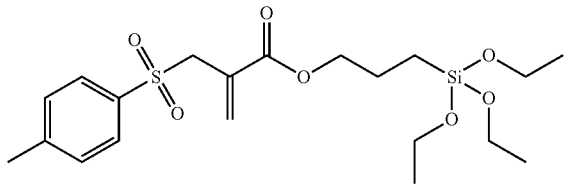 [SMILES: C=C(CS(=O)(=O)c1ccc(C)cc1)C(=O)OCCC[Si](OCC)(OCC)OCC]

Under nitrogen, diisopropylethylamine (23.4 ml, 0.134 mol) was added dropwise to a solution of 2-(tosylmethyl) acrylic acid (29.36 g, 0.122 mol) and (3-iodopropyl)triethoxysilane (40.60 g, 0.122 mol) in dry acetonitrile (200 ml). The reaction mixture was stirred for 24 h at 80° C. and then concentrated in vacuo. After the addition of diethyl ether (200 ml) the salt precipitates, which is filtered off. The remaining filtrate is concentrated under reduced pressure and the residue is purified by means of column chromatography (eluent=ethyl acetate/heptane: 1/1). 34.04 g (63% yield) of a colourless oil is obtained.

$^1$H NMR (CDCl$_3$, 400 MHz): δ=0.53-0.62 (m, 2H, CH$_2$Si); 1.21 (t, $^3J_{HH}$=7.0 Hz, 9H, OCH$_2$CH$_3$); 1.61-1.71 (m, 2H, CH$_2$CH$_2$Si); 2.42 (s, 3H, C$_{Ar}$CH$_3$); 3.80 (q, $^3J_{HH}$=7.0 Hz, 6H, OCH$_2$CH$_3$); 3.92 (t, $^3J_{HH}$=6.9 Hz, 2H, CH$_2$OCO); 4.11 (s, 2H, CH$_2$S); 5.87 (s, 1H, C=CH$_2$); 6.47 (s, 1H, C=CH$_2$); 7.28-7.33 (m, 2H, CH$_{Ar}$); 7.68-7.73 (m, 2H, CH$_{Ar}$). $^{13}$C NMR (CDCl$_3$, 101 MHz): δ=6.5 (CH$_2$Si); 18.3 (OCH$_2$CH$_3$); 21.6 (C$_{Ar}$CH$_3$); 22.0 (CH$_2$CH$_2$Si); 57.5 (CH$_2$S); 58.4 (OCH$_2$CH$_3$); 67.5 (CH$_2$OCO); 128.7 (CH$_{Ar}$); 129.2 (C=CH$_2$); 129.6 (CH$_{Ar}$); 133.1 (C=CH$_2$); 135.5 (C$_{Ar}$); 144.9 (C$_{Ar}$); 164.8 (C=O). $^{29}$Si NMR (CDCl$_3$, 79 MHz): −46.2.

Example 4

Hydrolytic Condensation of 3-(triethoxysilyl)-propyl-2-(tosylmethyl) acrylate

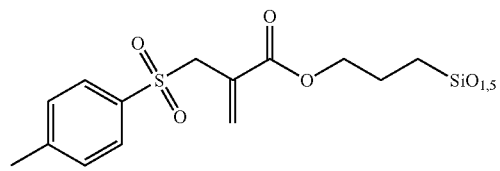

A solution of 3-(triethoxysilyl)-propyl-2-(tosylmethyl) acrylate (8.91 g, 20.0 mmol) in ethanol (110 ml) was mixed with hydrochloric acid (0.55 M, 1.07 g, 60 mmol) and stirred for 72 h at ambient temperature. The solvent was removed and the residue was dried at 60° C. in a fine vacuum. 6.35 g (95% yield) of a highly viscous yellowish oil that is insoluble in water was obtained.

$^1$H-NMR (CDCl$_3$, 400 MHz): δ=0.68-0.77 (m, 2H; Si—CH$_2$), 1.61-1.74 (m, 2H; CH$_2$—CH$_2$—CH$_2$), 2.43 (s, 3H; CH$_3$), 3.79-3.82 (m, 2H; O—CH$_2$), 4.04-4.12 (m, 4H; SO$_2$—O—CH$_2$), 5.73-5.83 (m, 1H; =CH), 6.46 (s, 1H; =CH), 7.32 (d, 2H; Ar—H), 7.72 (d, 2H; Ar—H).

Example 5

Silanization of Fumed Silica with the Silane 3-(triethoxysilyl)-propyl-2-(tosylmethyl) acrylate from Example 3

To a suspension of 10.0 g fumed silica (specific surface area 35-65 m$^2$/g, Aerosil® OX50, Evonik) in 100 ml cyclohexane was slowly added dropwise 2.31 g (5.20 mmol) 3-(triethoxysilyl)-propyl-2-(tosylmethyl) acrylate and then 0.332 g (5.61 mmol) n-propylamine. The suspension was stirred for 24 h at 20° C. and then centrifuged at 3000 rpm. After decanting off the cyclohexane, the precipitate was washed twice more with cyclohexane and in each case centrifuged. The obtained solid was dried in a Rotavapor at 40° C./0.1 mbar for 48 h and then sieved (90 μm). 7.08 g of a white powder that is insoluble in water was obtained (residue on ignition: 90.6%, blank value OX50: 99.1%).

Example 6

Production and Photo Polymerization of Methacrylate Resins with the Condensate from Example 2

A mixture of the urethane dimethacrylate RM-3 (addition product of 2 mol 2-hydroxyethyl methacrylate and 1 mol 2,2,4-trimethylhexamethylene diisocyanate) and triethylene gylcol dimethacrylate (TEGDMA) in the weight ratio 1:2 was produced. To this were added 0.3 wt.-% Ivocerin® (bis(4-methoxybenzoyl)diethylgermanium, Ivoclar Vivadent AG) and 5.0 wt.-% AFCT reagent as photoinitiator. The condensate from Example 2 was used as AFCT reagent and 2-(toluene-4-sulfonyloxy)acrylic acid ethyl ester TSAEE was used as reference vinyl sulfone ester. Corresponding test pieces were prepared from the photopolymerization resins, which were irradiated 2 times for 3 minutes with a dental light source (Spectramat®, Ivoclar Vivadent AG) and thereby cured. The determination of the flexural strength and the flexural modulus of elasticity was carried out in accordance with the ISO standard ISO-4049 (Dentistry—Polymer-based filling, restorative and luting materials) after 24 h storage of the test pieces in water. An improvement in the mechanical properties was exhibited when the AFCT reagent was used as condensate (see Table 1).

TABLE 1

Photopolymer properties

| Photopolymer | Flexural strength (MPa) | Flexural modulus of elasticity (GPa) |
| --- | --- | --- |
| A (without AFCT reagent)* | 81.0 | 1.82 |
| B (with condensate Ex. 2) | 91.5 | 2.07 |
| C (with TSAEE)* | 83.9 | 1.91 |

*Comparison example

In addition, the test pieces were ground in a mortar and the polymers in powder form were dispersed in aqueous ethanol (50 vol.-% ethanol). After 72 h stirring, the solid portions were separated off and examined in the liquid residue by means of HPLC. It was shown that portions of the AFCT reagent TSAEE could be washed out of reference polymer C, while no AFCT reagent could be detected in the eluate of sample B.

Example 7

Production and Photo Polymerization of Methacrylate Resins with the Condensate from Example 4

A mixture of the urethane dimethacrylate RM-3 and TEGDMA in the weight ratio 1:2 was produced. To this were added 0.3 wt.-% Ivocerin® and 5 wt.-% AFCT reagent as photoinitiator. The condensate from Example 4 was used as AFCT reagent and 2-(toluene-4-sulfonylmethyl)acrylic acid ethyl ester TSMAEE was used as reference allyl sulfone. Corresponding test pieces were prepared from the photopolymerization resins, which were irradiated 2 times for 3 minutes with a dental light source (Spectramat®, Ivoclar Vivadent AG) and thereby cured. The determination of the flexural strength and the flexural modulus of elasticity was carried out in accordance with the ISO standard ISO-4049 (Dentistry—Polymer-based filling, restorative and luting materials) after 24 h storage of the test pieces in water.

TABLE 2

Photopolymer properties

| Photopolymer | Flexural strength (MPa) | Flexural modulus of elasticity (GPa) |
| --- | --- | --- |
| D (without AFCT reagent)* | 81.0 | 1.82 |
| E (with condensate Ex. 4) | 84.7 | 1.90 |
| F (with TSMAEE)* | 73.0 | 1.68 |

*Comparison example

Here too, an improvement in the mechanical properties was exhibited when the AFCT reagent was used as condensate (see Table 2).

In addition, the test pieces were ground in a mortar and the polymers in powder form were dispersed in aqueous ethanol (50 vol.-% ethanol). After 72 h stirring, the solid portions were separated off and examined in the liquid residue by means of HPLC. It was shown that portions of the AFCT reagent TSAEE could be washed out of reference polymer F, while no AFCT reagent could be detected in the eluate of sample E.

The invention claimed is:

1. Radically polymerizable silane according to the general formula I

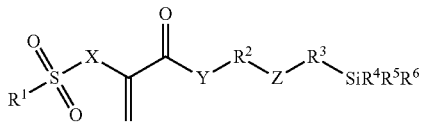

Formula I in which
R$^1$ is a linear or branched aliphatic C$_1$-C$_9$-alkyl radical, phenyl or alkylated phenyl radical,
R$^2$, R$^3$ independently of each other in each case are absent or are a linear or branched aliphatic C$_1$-C$_{20}$-alkylene radical, which can be interrupted by S or O atoms,
R$^4$, R$^5$, R$^6$ independently of each other in each case are —Cl, —O—CH$_3$, —O—C$_2$H$_5$, —CH$_3$ or —C$_2$H$_5$,
X is CH$_2$ or O,
Y is absent, or is O or NR', wherein R' is H or a C$_{1-5}$-alkyl radical, and
Z is absent, or is O, NR'', —CO—O—, —CO—NR''—, —O—CO—O—, —O—CO—NR''—, or —NR''—CO—NR''—, wherein R'' is H or a C$_{1-5}$-alkyl radical and wherein the radicals R$^2$ and R$^3$ cannot be absent at the same time and Z is absent if R$^2$ or R$^3$ is absent.

2. Radically polymerizable silane according to claim 1, wherein
R$^1$ is —CH$_3$, —C$_2$H$_5$, phenyl or tolyl,
R$^2$, R$^3$ independently of each other in each case are absent or are a linear aliphatic C$_1$-C$_{10}$-alkylene radical, which can be interrupted by O atoms,
R$^4$, R$^5$, R$^6$ independently of each other in each case are —O—CH$_3$ or —O—C$_2$H$_5$,
X is CH$_2$ or O,
Y is absent or is O, and
Z is absent, or is O, —CO—O—, —CO—NH—, —O—CO—O— or —O—CO—NH—.

3. Radically polymerizable silane according to claim 1, wherein
R$^1$ is —CH$_3$, —C$_2$H$_5$, phenyl or tolyl,
R$^2$ is a linear aliphatic C$_2$-C$_8$-alkylene radical, which can be interrupted by O atoms,
R$^3$ is absent or is a linear aliphatic C$_1$-C$_6$-alkylene radical,
R$^4$, R$^5$, R$^6$ independently of each other in each case are —O—CH$_3$ or —O—C$_2$H$_5$,
X is CH$_2$ or O,
Y is O, and
Z is absent, or is —CO—NH— or —O—CO—NH—.

4. Process for the production of polysiloxane condensates, in which at least one silane according to claim 1 is mixed with a stoichiometric amount or an excess of water and the mixture is then allowed to react.

5. Process according to claim 4, in which the silane is dissolved in an organic solvent, the solution is then mixed with water or a mixture of water and an organic solvent, the mixture is then allowed to react at a temperature in the range of from 0° C. to 140° C. and the solvent and volatile components are subsequently removed.

6. Process according to claim 4, in which the mixture is additionally mixed with a catalyst.

7. Process according to claim 6, in which the catalyst comprises an acid selected from acetic acid or hydrochloric acid or a base selected from ammonia, amine, NaOH, methylimidazole, or ammonium fluoride.

8. Process for the production of a surface-modified filler, in which a filler is dispersed in an organic solvent, the dispersion is mixed with at least one silane according to claim 1, water and a catalyst and stirred, and the filler is subsequently separated from the solvent.

9. Process according to claim 8, in which the filler comprises an inorganic particulate filler, an X-ray opaque filler, an amorphous spherical filler based on an oxide, and/or a fibrous filler.

10. Process according to claim 9, in which the inorganic particulate filler comprises quartz powder, barium or strontium aluminium silicate glass powder, the X-ray opaque filler comprises ytterbium trifluoride, the amorphous spherical filler based on an oxide comprises fumed silica, precipitated silica, $ZrO_2$, ZnO, $TiO_2$ or a mixed oxide made of $SiO_2$, $ZrO_2$ and/or $TiO_2$, particulate tantalum(V) oxide, barium sulfate or a mixed oxide of $SiO_2$ with ytterbium(III) oxide or tantalum(V) oxide, and the fibrous filler comprises nanofibres, glass fibres, polyamide or carbon fibres.

11. Process according to claim 8, in which the mixture is stirred at a temperature in the range of from 0 to 100° C. for 1 to 20 hours.

12. Polysiloxane condensate, which is obtained according to the process according to claim 4.

13. Surface-modified filler, which is obtained according to the process according to claim 8.

14. Dental material comprising a silane, polysiloxane condensate and/or a surface-modified filler,
wherein the silane comprises

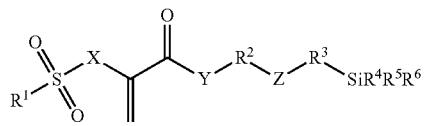

Formula I in which
R$^1$ is a linear or branched aliphatic $C_1$-$C_9$-alkyl radical, phenyl or alkylated phenyl radical,
R$^2$, R$^3$ independently of each other in each case are absent or are a linear or branched aliphatic $C_1$-$C_{20}$-alkylene radical, which can be interrupted by S or O atoms,
R$^4$, R$^5$, R$^6$ independently of each other in each case are —Cl, —O—CH$_3$, —O—C$_2$H$_5$, —CH$_3$ or —C$_2$H$_5$,
X is CH$_2$ or O,
Y is absent, or is O or NR', wherein R' is H or a $C_{1-5}$-alkyl radical, and
Z is absent, or is O, NR", —CO—O—, —CO—NR"—, —O—CO—O—, —O—CO—NR"—, or —NR"—CO—NR"—, wherein R" is H or a $C_{1-5}$-alkyl radical and wherein the radicals R$^2$ and R$^3$ cannot be absent at the same time and Z is absent if R$^2$ or R$^3$ is absent,
wherein the polysiloxane condensate comprises the silane mixed with a stoichiometric amount or an excess of water and the mixture is then allowed to react, and
wherein the surface-modified filler comprises a filler dispersed in an organic solvent, the dispersion is mixed with the silane, water and a catalyst and stirred, and the filler is subsequently separated from the solvent.

15. Dental material according to claim 14, which contains
(a) 1 to 50 wt.-% of at least one silane of Formula I, at least one polysiloxane condensate, and/or at least one surface-modified filler,
(b) 0.01 to 5 wt.-% of at least one initiator for radical polymerization and
(c) 5 to 80 wt.-% of at least one radically polymerizable monomer, in each case based on the total mass of the material.

16. Dental material according to claim 14, which contains
(a) 2 to 40 wt.-% of at least one silane of Formula I, at least one polysiloxane condensate, and/or at least one surface-modified filler,
(b) 0.1 to 5 wt.-% of at least one initiator for radical polymerization and
(c) 10 to 60 wt.-% of at least one radically polymerizable monomer, in each case based on the total mass of the material.

17. Dental material according to claim 14, which contains
(a) 3 to 30 wt.-% of at least one silane of Formula I; at least one polysiloxane condensate, and/or at least one surface-modified filler,
(b) 1.0 to 3.0 wt.-% of at least one initiator for radical polymerization and
(c) 10 to 50 wt.-% of at least one radically polymerizable monomer, in each case based on the total mass of the material.

18. Dental material according to claim 15, which additionally contains
(d) 1 to 80 wt. % filler.

19. Method of using the silane according to claim 1 for the production of a dental material comprising combining the silane with at least one initiator for radical polymerization, at least one radically polymerizable monomer and optionally with at least one filler and/or additive.

20. Dental material according to claim 15, which additionally contains
(d) 10-70 wt.-% filler.

21. Method of using the polysiloxane according to claim 4 for the production of a dental material, comprising combining the polysiloxane with at least one initiator for radical polymerization, at least one radically polymerizable monomer and optionally with at least one filler and/or additive.

22. Method of using the surface-modified filler according to claim 8 for the production of a dental material, comprising combining the surface-modified filler with at least one initiator for radical polymerization, at least one radically polymerizable monomer and optionally with at least one filler and/or additive.

23. Dental material according to claim 15, which additionally contains
(d) 50-80 wt.-% filler.

* * * * *